United States Patent [19]

Farmer et al.

[11] Patent Number: 5,013,760
[45] Date of Patent: May 7, 1991

[54] PHENYLETHYLAMINE DERIVATIVES AND PHARMACEUTICAL USE

[75] Inventors: John B. Farmer, Cropston; Francis Ince; Rodney A. Brown, both of Loughborough; John Dixon, Belton, all of England

[73] Assignee: Fisons plc, Ipswich, England

[21] Appl. No.: 846,846

[22] Filed: Apr. 1, 1986

Related U.S. Application Data

[63] Continuation of Ser. No. 402,084, Jul. 26, 1982, Pat. No. 4,645,768.

[30] Foreign Application Priority Data

| Aug. 5, 1981 | [GB] | United Kingdom | 8123962 |
| Oct. 9, 1981 | [GB] | United Kingdom | 8130594 |
| Oct. 9, 1981 | [GB] | United Kingdom | 8130595 |
| Nov. 17, 1981 | [GB] | United Kingdom | 8134551 |

[51] Int. Cl.$^5$ .......................................... C07C 215/52
[52] U.S. Cl. .................................... 514/649; 564/367
[58] Field of Search ................. 564/369, 367; 514/649

[56] References Cited

U.S. PATENT DOCUMENTS

| 2,653,977 | 9/1953 | Craig et al. | 564/367 |
| 2,739,981 | 3/1956 | Szabo et al. | 564/367 X |
| 2,937,185 | 5/1960 | Biel | 564/367 X |
| 3,013,020 | 12/1961 | Fancher | 564/367 X |
| 3,867,454 | 2/1975 | Diana et al. | 564/367 |
| 3,928,323 | 12/1978 | Green et al. | 564/367 X |
| 3,933,913 | 1/1976 | Colella et al. | 564/367 X |
| 3,960,959 | 6/1976 | Pless | 564/367 |
| 4,645,768 | 2/1987 | Olejnik | 514/649 |

Primary Examiner—Richard L. Raymond
Attorney, Agent, or Firm—Marshall, O'Toole, Gerstein, Murray & Bicknell

[57] ABSTRACT

Phenylethylamine derivatives of the formula

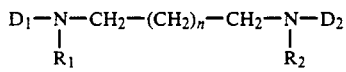

wherein
$D_1$ represents a phenylethyl radical which is substituted with hydroxy and/or alkyl groups,
$R_1$ and $R_2$ are hydrogen or alkyl,
$D_2$ represents hydrogen, an alkyl, or aryl group, and n is an integer from 3 to 5.

These compounds are useful as pharmaceuticals, e.g., for treatment of cardiovascular conditions.

5 Claims, No Drawings

PHENYLETHYLAMINE DERIVATIVES AND PHARMACEUTICAL USE

This application is a continuation of application Ser. No. 402,084, filed Jul. 26, 1982, now U.S. Pat. No. 4,645,768.

This invention relates to new compounds, processes for their preparation, and compositions containing them.

According to the invention we provide the compounds of formula I,

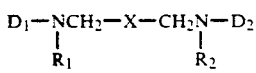

$$D_1-NCH_2-X-CH_2N-D_2 \quad\quad I$$
$$\phantom{D_1-NCH_2-X-CH_2N-}R_1 \phantom{XXXXXXX} R_2$$

in which $D_1$ represents a group of formula II,

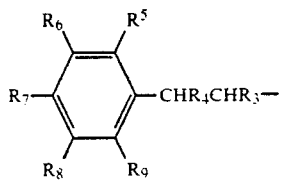

where $R_1$ and $R_5$, or $R_3$ and $R_5$ may form a chain —$CH_2CH_2$—, or $R_4$ and $R_5$ may form a chain —$CH_2$—, or $R_3$, $R_4$ and $R_5$ are each hydrogen, the remainder of $R_1$, $R_3$ and $R_4$, which may be the same or different, being hydrogen, alkyl or phenyl, none, one or two of $R_6$, $R_7$, $R_8$ and $R_9$ represent hydroxy and the remainder represent hydrogen, X represents a chain —$(CH_2)_n$—, optionally substituted by hydroxy, n is an integer from 1 to 7 inclusive, $D_2$ represents hydrogen, alkyl, phenyl; alkyl substituted by one or more of hydroxy, pyridyl, phenyl; or alkyl substituted by phenyl which in turn is substituted by halogen, alkyl, amino, alkoxy or nitro, or $D_2$ represents a group of formula III,

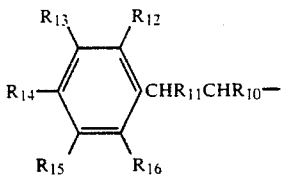

where $R_2$ and $R_{12}$, or $R_{10}$ and $R_{12}$ may form a chain —$CH_2$—$CH_2$—, or $R_{11}$ and $R_{12}$ may form a chain —$CH_2$—, or $R_{10}$, $R_{11}$ and $R_{12}$ are each hydrogen, the remainder of $R_2$, $R_{10}$ and $R_{11}$, which may be the same or different being hydrogen, alkyl or phenyl, none, one or two of $R_{13}$, $R_{14}$, $R_{15}$ and $R_{16}$ represent hydroxy, and the remainder represent hydrogen, or $R_2$ and $D_2$, together with the nitrogen atom to which they are attached, form a 5 or 6 membered heterocyclic ring, provided that when X is not substituted by hydroxy and (i) when $R_3$, $R_4$ and $R_5$ are hydrogen, $R_1$ and $R_2$ are both hydrogen or lower alkyl, and two of $R_6$, $R_7$, $R_8$ and $R_9$ are hydroxy, $D_2$ is not identical to $D_1$, or (ii) when $R_1$, $R_3$, $R_4$, $R_5$, $R_6$, $R_7$, $R_8$ and $R_9$ are hydrogen, $R_2$ and $D_2$ do not each represent lower alkyl, or do not together with the nitrogen atom to which they are attached, form a 5 or 6 membered heterocyclic ring, or (iii) when $R_1$, $R_4$, $R_5$, $R_6$, $R_7$, $R_8$ and $R_9$ are hydrogen, and $R_3$ is alkyl, $D_2$ is not identical to $D_1$, or (iv) when $R_1$ is phenyl, $R_3$ and $R_5$ together form the chain —$CH_2CH_2$—, $R_6$, $R_7$, $R_8$ and $R_9$ are hydrogen, n is 1, $D_2$ and $R_2$ do not each represent hydrogen or alkyl, or do not together form a heterocyclic ring, and pharmaceutically acceptable derivatives thereof.

The invention also provides the compounds of formula I, and their pharmaceutically acceptable derivatives, as pharmaceuticals.

According to our invention we also provide a process for the production of a compound of formula I, or a pharmaceutically acceptable derivative thereof, which comprises (a) selectively reducing a compound of the formula IV,

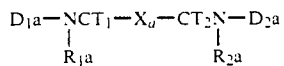

$$D_{1a}-NCT_1-X_a-CT_2N-D_{2a} \quad\quad IV$$
$$\phantom{D_{1a}-NCT_1-}R_{1a} \phantom{XXXXXXX} R_{2a}$$

in which both $T_1$ and $T_2$ represent $H_2$ or 0, provided that at least one of $T_1$ and $T_2$ represents 0;

$R_{1a}$ and $R_{2a}$ have the same significance as $R_1$ and $R_2$ above, save that in addition they may represent a protecting group, $D_{1a}$ represents a group of formula V,

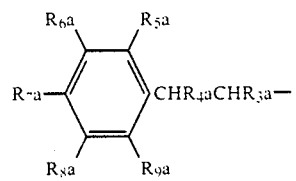

where $R_{3a}$, $R_{4a}$, $R_{5a}$, $R_{6a}$, $R_{7a}$, $R_{8a}$ and $R_{9a}$ respectively have the same significances as $R_3$, $R_4$, $R_5$, $R_6$, $R_7$, $R_8$ and $R_9$ above, save that in addition one or two of $R_{6a}$, $R_{7a}$, $R_{8a}$ and $R_{9a}$ may represent a protected hydroxy group, $X_a$ has the same significance as X above, save that in addition it may bear a protected hydroxy, $D_{2a}$ represents hydrogen, alkyl, phenyl; or alkyl substituted by one or more of hydroxy, protected hydroxy, pyridyl, phenyl; or alkyl substituted by phenyl which in turn is substituted by halogen, alkyl, amino, alkoxy or nitro;

or $D_{2a}$ represents a group of formula VI,

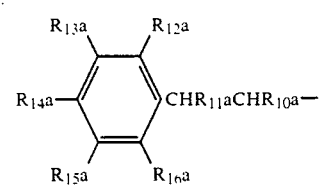

where $R_{10a}$, $R_{11a}$, $R_{12a}$, $R_{13a}$, $R_{14a}$, $R_{15a}$ and $R_{16a}$ respectively have the same significance as $R_{10}$, $R_{11}$, $R_{12}$, $R_{13}$, $R_{14}$, $R_{15}$ and $R_{16}$ above, save that in addition one or more of $R_{13a}$, $R_{14a}$, $R_{15a}$ and $R_{16a}$ may represent a protected hydroxyl group, and, if necessary or desired thereafter, removing any protecting groups to give the corresponding compound of formula I, (b) producing a compound of formula I in which $D_2$ is identical to $D_1$, and $R_1$ is identical to $R_2$, by reacting a compound of formula VII,

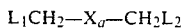

$$L_1CH_2-X_a-CH_2L_2 \qquad VII$$

in which $L_1$ and $L_2$, which may be the same or different, represent leaving groups, $X_a$ is as defined above, with a compound formula VIII,

$$\begin{array}{c} D_1b-NH \\ | \\ R_1b \end{array} \qquad VIII$$

or an acid addition salt thereof, $D_1b$ represents the group of formula IX,

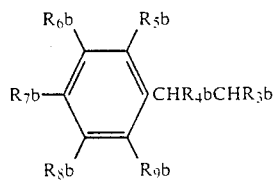

in which $R_1b$, $R_3b$, $R_4b$, $R_5b$, $R_6b$, $R_7b$, $R_8b$ and $R_9b$ respectively have the same significances as $R_1$, $R_3$, $R_4$, $R_5$, $R_6$, $R_7$, $R_8$ and $R_9$ above, save that in addition $R_1b$ may represent a removable group capable of increasing the nucleophilicity of nitrogen, and one or two of $R_6b$, $R_7b$, $R_8b$ and $R_9b$ may represent a protected hydroxy, and if necessary or desired thereafter, removing any such protecting or removable groups to give the corresponding compound of formula I, (c) producing a compound of formula I in which $D_2$ is identical to $D_1$ and both $R_3$ groups are hydrogen, by selectively reducing a compound of formula X,

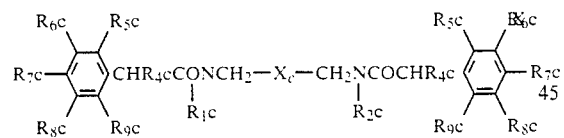

in which $R_1c$, $R_2c$, $R_4c$, $R_5c$, $R_6c$, $R_7c$, $R_8c$, $R_9c$ and $X_c$ respectively have the same significances as $R_1$, $R_2$, $R_4$, $R_5$, $R_6$, $R_7$, $R_8$, $R_9$ and X above, save that in addition, either one or both of $R_1c$ and $R_2c$ may represent protecting groups, one or two of $R_6c$, $R_7c$, $R_8c$ and $R_9c$ may represent a protected hydroxy group, and $X_c$ may bear a protected hydroxy group, and if necessary or desired thereafter removing any such protecting groups to give the corresponding compound of formula I, or (d) removal of a protecting group from a corresponding compound of formula I carrying one or more protected hydroxy or protected amine groups, and where desired or necessary converting the resulting compound of formula I to a pharmaceutically acceptable derivative thereof, or vice versa.

In process (a), the reducing agent may be electrophilic, for example diborane, or nucleophilic, for example a complex metal hydride, e.g. lithium aluminum hydride or sodium (2-methoxyethoxy)aluminum hydride. The solvent is preferably inert to the reaction conditions. Aprotic solvents are preferred, for example tetrahydrofuran, diethyl ether, or 1,2-dimethoxyethane. The reaction may be carried out at a temperature of from about 0° to 100° C.

When $R_1a$ and/or $R_2a$ represent a protecting group, the protecting group may be a hydrogenolisable protecting group, for example, a 1-phenylalkyl derivative, e.g. benzyl. The protecting group may be removed by reduction using, e.g. hydrogen and a suitable hydrogenation catalyst, e.g. palladium on charcoal.

When one or two of $R_6a$, $R_7a$, $R_8a$ and $R_9a$ represents a protected hydroxy group and/or $D_2a$ carries a protected hydroxy group, the protected hydroxy group may be, for example alkoxy, phenylalkoxy, e.g. phenylmethoxy, or alkanoyloxy, e.g. acetoxy.

Removal of the hydroxy protecting groups depends on the nature of the protecting group, but conventional techniques may generally be employed, including acidic and basic cleavage, and hydrogenolysis. For example, protecting alkyl or phenyl alkyl groups may be removed by cleavage using a protic acid, e.g. hydrochloric acid or hydrobromic acid at 0° to 150° C., or a Lewis acid, e.g. by reacting with a boron trihalide in a chlorocarbon solvent. When the protecting group is alkanoyl, cleavage may be effected using a base, e.g. sodium hydroxide, in a suitable solvent, e.g. aqueous ethanol Lewis bases, e.g. pyridine hydrochloride may be used to cleave alkyl or phenylalkyl groups 1-Phenylalkyl groups, e.g. benzyl, may be removed by catalytic hydrogenation using a suitable catalyst, e.g. palladium, in a suitable solvent, e.g. ethanol, or acetic acid, preferably under pressure In process (b) $L_1$ and $L_2$ may be an anion forming group, for example, halogen, e.g. chlorine or bromine, or p-toluenesulphonate. The reaction is preferably carried out in a suitable solvent in the presence of a base. The solvent may also act as the base Suitable solvents, are for example, pyridine (in which case, no added base is necessary), or ethanol or dimethylformamide (with which a base, for example pyridine, triethylamine or sodium hydroxide is preferably used). The reaction may be carried out at a temperature of from about 0° to 100° C.

When $R_1b$ represents a removable group capable of increasing the nucleophilicity of nitrogen, $R_1b$ may be, for example, p-toluenesulphonyl, or trihaloacetyl, e.g. trichloroacetyl or trifluoroacetyl.

The removal of protecting groups in process (b) may be carried out as described for process (a).

The reduction, and removal of protecting groups, in process (c) may be carried out as described for process (a).

The removal of protecting groups in process (d) may be carried out as described for process (a), under acidic, basic or hydrogenolytic conditions When $D_2$ of formula I represents an alkyl group substituted by phenyl substituted by amino, the amino group may be obtained by reduction of a suitably placed nitro protecting group, using for example, catalytic hydrogenation, e.g. hydrogen and palladium, in a suitable solvent, e.g. ethanol, preferably at an elevated pressure, or chemical reduction, e.g. using tin and a suitable acid, e.g. hydrochloric acid, at a temperature of from about 0° to 100° C.

When $D_1a$ equals $D_2a$, and $R_1a$ equals $R_2a$, and both $T_1$ and $T_2$ equal=0, the compounds of formula IV may be prepared by reacting a compound of formula XI, $$Z_1CO-X_a-COZ_2 \quad \text{XI}$$

where $Z_1$ and $Z_2$, which may be the same or different, represent good leaving groups,
$X_a$ is defined above,
with a compound of formula XII,

  XII in which $D_{1a}$ and $R_{1a}$ are as defined above.

Good leaving groups $Z_1$ and $Z_2$ include, for example, halogen, e.g. chlorine, bromine, 1-imidazolyl, trifluromethane sulphonate, alkyl carbonate, e.g. ethyl or benzyl carbonate, or alkanoyloxy, e.g. trifluoroacetoxy.

The reaction may be carried out in a solvent which is inert to the reaction conditions, for example, a chlorinated hydrocarbon, e.g. chloroform, in the presence of a non-nucleophilic base, e.g. triethylamine. The reaction may be carried out at a temperature of from about 0° to 100° C.

The free acid corresponding to formula XI, i.e. when $Z_1$ and $Z_2$ both equal hydroxy, may be reacted, e.g. with thionyl chloride, ethyl chloroformate or N,N'-carbonyldiimidazole to convert the COOH group to a group $-COZ_1$.

The compound of formula IV when $D_{2a}$ may or may not equal $D_{1a}$ and/or $R_{1a}$ may or may not equal $R_{2a}$ may be prepared by sequentially reacting the groups $Z_1$ and $Z_2$, in any order in the molecule of formula XIII, $$Z_1CT_1-X_a-CT_2Z_2 \quad \text{XIII}$$

in which $T_1$, $T_2$, $X_a$, $Z_1$ and $Z_2$ are as defined above, by reaction with a compound of formula XII and/or XIV,

  XIV where $D_{2a}$ and $R_{2a}$ are as defined above, as appropriate, followed by reaction of the resulting compound with a compound of formula XII or XIV.

The compounds of formula X may be prepared by reacting a compound of formula XV,

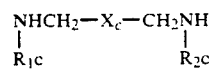  XV where $R_{1c}$, $R_{2c}$ and $X_c$ are as defined above, with a compound of formula XVI,

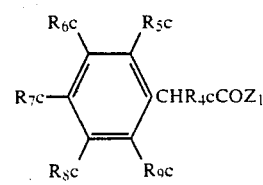  XVI where $Z_1$, $R_{4c}$, $R_{5c}$, $R_{6c}$, $R_{7c}$, $R_{8c}$ and $R_{9c}$ are as defined above.

The reaction may be carried out under the same conditions as the reaction of compounds of formula XI and XII above.

The free acid corresponding to formula XVI may be reacted with the same reagents and in the same manner as the free acid corresponding to formula XI to produce the required starting material.

The compounds of formula VII, VIII, the free acid corresponding to formula XI, XII, XIII, XIV, XV and the free acid corresponding to formula XVI are either known, or may be made from known compounds using techniques known per se.

When any of the starting materials or intermediates contain a chiral center, they may be resolved using conventional techniques.

The acid addition salts of the compound of formula I may be prepared by reaction of the free-base with an appropriate acid. The acid addition salts may be converted to the corresponding free-base by the action of a stronger base.

The processes as described above may produce the compound of formula I or a derivative thereof. It is also within the scope of this invention to treat any derivative so produced to liberate the free compound of formula I, or to convert one derivative into another.

The compounds of formula I and the intermediates therefore may be isolated from their reaction mixtures using conventional techniques.

Pharmaceutically acceptable derivatives of the compounds of formula I include pharmaceutically acceptable acid addition salts. Suitable salts include salts of mineral acids, for example, hydrohalic acids, e.g. hydrochloric acid or hydrobromic acid, or organic acids, e.g. formic, acetic or lactic acids. The acid may be polybasic, for example sulfuric, fumaric or citric acid.

Other pharmaceutically acceptable derivatives are compounds which will be suitable bioprecursors (prodrugs) of the compounds of formula I and will be readily apparent to those skilled in the art and may be made from the compounds of formula I using conventional processes known per se or by processes analogous to those described above. Suitable bioprecursors include amides of compounds of formula I, and when a compound of formula I bears a hydroxy group, esters for example carboxylic acid esters, e.g. alkanoyl, such as acetyl or isobutyl, or aroyl, e.g. benzoyl.

We prefer each of $R_1$, $R_2$, $R_4$ and $R_{11}$ when they represent alkyl, to contain up to and including 8, and preferably up to and including 4 carbon atoms.

As a specific group we provide compounds of formula I in which one or both of $R_1$ and $R_2$ is, hydrogen or alkyl Cl-6, for example methyl or n-propyl, or $R_1$ and $R_5$, or $R_2$ and $R_{12}$ form respectively part of the groups $A_1$ or $A_2$,

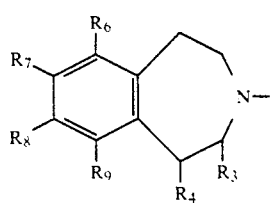  $A_1$

-continued

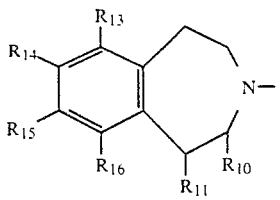
A₂ where $R_3$, $R_4$, $R_6$, $R_7$, $R_8$, $R_9$, $R_{10}$, $R_{11}$, $R_{13}$, $R_{14}$, $R_{15}$ and $R_{16}$ are as defined above.

As a further specific group we provide compounds of formula I in which one or both of $R_3$ and $R_{10}$ is hydrogen, or $R_3$ and $R_5$, or $R_{10}$ and $R_{12}$, form respectively part of the groups $B_1$ or $B_2$,

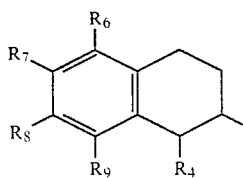 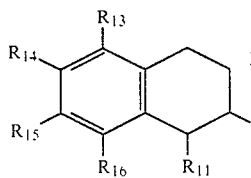

where $R_4$, $R_6$, $R_7$, $R_8$, $R_9$, $R_{11}$, $R_{13}$, $R_{14}$, $R_{15}$ and $R_{16}$ are as defined above.

As a still further specific group we provide compounds of formula II in which one or both of $R_4$ and $R_{11}$ is, hydrogen, hydroxy or phenyl or $R_4$ and $R_5$, or $R_{11}$ and $R_{12}$, form respectively part of the groups $C_1$ or $C_2$,

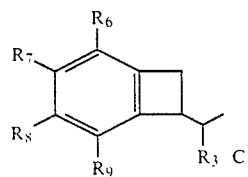 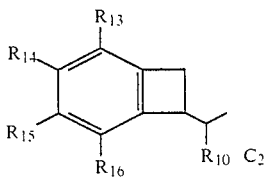

where $R_3$, $R_6$, $R_7$, $R_8$, $R_9$, $R_{10}$, $R_{13}$, $R_{14}$, $R_{15}$ and $R_{16}$ are as defined above.

As a yet further group we provide compounds of formula I in which all of $R_3$, $R_4$ and $R_5$, or all of $R_{10}$, $R_{11}$ and $R_{12}$ are hydrogen, and form respectively part of the groups $E_1$ and $E_2$,

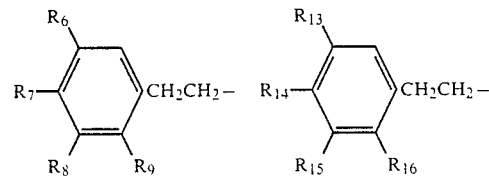

where $R_6$, $R_7$, $R_8$, $R_9$, $R_{13}$, $R_{14}$, $R_{15}$ and $R_{16}$ are as defined above.

We prefer at least one, and preferably two, of $R_6$, $R_7$, $R_8$ and $R_9$ to be hydroxy.

We prefer at least one, and preferably two, of $R_{13}$, $R_{14}$, $R_{15}$ and $R_{16}$ to be hydroxy.

We particularly prefer an adjacent pair of $R_6$, $R_7$, $R_8$ and $R_9$, and/or an adjacent pair of $R_{13}$, $R_{14}$, $R_{15}$ and $R_{16}$ to both be hydroxy.

We specifically prefer compounds in which $R_7$ is hydroxy.

We prefer n to be from 2 to 6 inclusive, preferably to be from 3 to 5 inclusive and especially to be 4.

When $D_2$ represents alkyl, or optionally substituted alkyl, the alkyl moiety may contain up to and including 8, and preferably up to and including 4 carbon atoms.

When $D_2$ represents alkyl substituted by an optionally substituted phenyl, the optionally substituted phenyl moiety may contain from 6 and up to and including 10 carbon atoms.

When $R_2$ and $D_2$, together with the nitrogen to which they are attached form a 5 or 6 membered heterocyclic ring, the ring may be pyrrolidino, piperidino, morpholino or particularly piperazino. When the ring is piperazino, the 4-nitrogen may be substituted with alkyl C1-6, e.g methyl.

We especially prefer compounds of formula 1 which contain the following pairs of groups, $A_1$ and $E_2$, $B_1$ and $B_2$, $B_1$ and $E_2$, $C_1$ and $C_2$, $C_1$ and $E_2$, and $E_1$ and $E_2$, where $A_1$, $A_2$, $B_1$, $B_2$, $C_1$, $C_2$, $E_1$ and $E_2$ are as defined above.

Specifically preferred compounds of formula I are those of Examples 1, 5, 12, 14 and 22 and the pharmaceutically acceptable acid addition salts thereof.

Certain compounds of formula I can exist in optically active and meso forms. The invention also provides the optical isomers and meso isomers of these compounds of formula I, and mixtures, including racemic mixtures thereof. These compounds may be resolved into their optical isomers using conventional techniques.

When the carbon atom bearing $R_3$, $R_4$, $R_{10}$ or $R_{11}$ is in a chiral environment, the configuration of the carbon atom may be R or S. When two carbon atoms are in chiral environments, the compounds of formula I may be RR, RS, SR or SS, with respect to these two centers, except that when X is not chiral, $D_2$ equals $D_1$, and $R_2$ equals $R_1$, in which case the compounds of formula I may have RR, SS or meso configurations.

The compounds of formula I, and pharmaceutically acceptable derivatives thereof, are useful because they possess pharmacological activity in animals. Thus the compounds act on peripheral and/or central dopamine receptors. As such, they lower blood pressure, reduce heart rate and increase blood flow to certain vascular beds, e.g. renal beds. Some compounds also have an action on other adrenoreceptors, and these exhibit cardiac stimulant and bronchodilator effects. Activity of the compounds has been observed in the following assay systems:

(a) canine renal blood flow, McNay and Goldberg, J. Pharmac, Exp. Ther., 151, 23-31, 1966.

(b) rabbit isolated ear artery, McCullogh, Rand and Story, Br. J. Pharmac, 49, 141-142, 1973, and (c) cat nictitating membrane, Gyorgy and Doda, Arch. Int. Pharmacodyn, 226, 194-206, 1977.

The compounds of the invention are indicated for use in the treatment of congestive heart failure, renal failure, angina pectoris, ischaemic heart disease, hypertension and reversible obstructive airways disease, hyperprolactinaemia and also in Parkinson's disease and other neurological disorders.

The dosage administered will naturally depend on the compound employed, the mode of administration and the desired effect. However, in general, satisfactory results are obtained when the compounds are administered at a dosage of from 0.05 μg to 50 mg per kilogram of body weight per day. For man, the indicated total daily dosage is in the range 2.5 μg to 3.5 mg, which may be administered in divided doses of, for example 1 μg to 750 mg.

The new compounds of the present invention may be used in combination with or sequentially with a wide variety of other pharmaceutically active substances. Where appropriate the compounds may be mixed with one or more other active substances or may be chemically linked with the other active substance(s), e.g. to form a salt or ester. The particular mixture, dose regimen or chemically linked substance used, and ratio of the active ingredients will depend on a variety of factors including the condition to be treated, the mode of administration, the particular active ingredients and the patient concerned.

Examples of compounds with which the present compounds may be mixed or chemically linked include:

beta-blockers, especially cardioselective beta blockers, for example, atenelol, propanolol;
    diuretics, for example thiazides, e.g. furosemide;
    acetylcholinesterase inhibitors, for example captopril;
    inotropic agents, for example, amrinone;
    antiemetics, for example, sulpiride, metoclopramide, or domperidone.

The compounds of formula I, and pharmaceutically acceptable derivatives thereof, have the advantage that they are more efficacious or produce less undesirable side effects in certain pharmacological models, or are longer acting than compounds of similar structure to the compounds of formula I.

The compounds of the invention may be administered by a wide variety of routes and may act systemically or locally. Thus the compounds may be administered by oral or nasal inhalation to the lung, to the buccal cavity, oesophageally, rectally, topically to the skin or to other available surfaces of the body by injection, e.g. intravenously, intramuscularly, intraperitoneally, or by surgical implant.

According to our invention we also provide a pharmaceutical composition comprising preferably less than 80% and more preferably less than 50% by weight of a compound of formula I, or a pharmaceutically acceptable derivative thereof, in admixture with a pharmaceutically acceptable adjuvant, diluent or carrier. Examples of suitable adjuvants, diluents or carriers are: for tablets, capsules and degrees; microcrystalline cellulose, calcium phosphate, diatomaceous earth, a sugar such as lactose, dextrose or mannitol, talc, stearic acid, starch, sodium bicarbonate and/or gelatin;
    for suppositories; natural or hardened oil or waxes; and
    for inhalation compositions, coarse lactose.

When the compounds are to be used in aqueous solution it may be necessary to incorporate a chelating or sequestering agent, e.g. sodium edetate, an antioxidant, e.g. sodium metabisulphite or buffering agents, e.g. sodium hydrogen phosphate and sodium phosphate. Aqueous solutions typically contain up to about 10% w/w of the new compound and may be used for intravenous injections.

According to the invention, we further provide a method of increasing the force of contraction of the heart in an animal, either human or non-human, which method comprises administering to the animal an effective amount of one or more compounds of the invention.

The invention is illustrated, but in no way limited by the following examples. All temperatures quoted are in °C.

Stereochemical nomenclature is according to Appendix IV, selection of Index Names for Chemical Substances from the Chemical Abstracts 1977 Index Guide, paragraphs 202-212.

Assignments of absolute sterochemistry are based on the observations of Helmchen et al: (a) Tet. Letter 3873 (1972), (b) ibid 1527 (1974), (c) ibid 1417 (1977), and McDermed: Proceedings of the Symposium on Dopamine Agonists (Stockholm, 1982), Swedish Pharmaceutical Press.

EXAMPLES

Example 1

(R*S*)-2.2'[1,6-Hexanediylbisamino]-bis-[1,2,3,4-tetrahydro -5,6-naphthalenediol (a)

N-[1,2,3,4-Tetrahydro-5,6-dimethoxy-2-naphthylidene]-(R)-1-phenylethylamine

A solution of 1,2,3,4-tetrahydro-5,6-dimethoxy-2-tetralone (20.6 g) and (R)-1-phenylethylamine (14 ml) in dry toluene (200 ml) was heated under reflux for 4 hours with continual removal of the water formed. The mixture was evaporated to leave a brown oil (30 g) M$^-$309.

(b) (RS &RR)1,2,3,4-Tetrahydro-5,6-dimethoxy-N-(1-phenyl ethyl) naphthalenamine hydrochloride A solution of the imine from step (a) (28 g) in dry ethanol (250 ml) was hydrogenated over Adam's catalyst (1 g) at atmospheric pressure and room temperature until no further uptake of hydrogen was observed (~2 days).

The solution was filtered and evaporated to leave an oil which dissolved in excess ethanolic HCl. The solution was evaporated to leave a dark solid which was purified by trituration with cold isopropanol (50 ml) to give a colorless solid (23 g).

The above diastereomeric amines were separated using High Pressure Liquid Chromatography (HPLC) on a silica column eluting with a mixture containing triethylamine in petroleum ether—dichloromethane (1% in 4:1).

The free base of each diastereomer was converted to its hydrochloride salt and crystallised to >99.8% diastereomeric purity (confirmed by HPLC).
b1. 1st eluted diastereomer 9.5 g mp 265°-267°
b2. 2nd eluted diastereomer 6.0 g mp 297° dec (c) S(−)
1,2,3,4-Tetrahydro-5,6-dimethoxy-2-naphthalenamine hydrochloride A solution of the amine b1 (6.95 g) in dry methanol (400 ml) was hydrogenated over a 10% Pd/C catalyst (2 g) at atmospheric pressure and room temperature for 24 hours. The solution was filtered and the filtrate evaporated to leave a solid which crystallised from ethanol as colorless prisms (3.8 g) mp 270° $[\alpha]^{28}_D = -60.1$ (C=0.15 CH$_3$OH).

(d) R(+)
1,2,3,4-Tetrahydro-5,6-dimethoxy-2-naphthalenamine hydrochloride

A solution of the amine b2 (6.95 g) in dry methanol (500 ml) was hydrogenated over a 10% Pd/C catalyst (2 g) at atmospheric pressure and room temperature for 78 hours. The solution was filtered and the filtrate evaporated to leave a solid which crystallised from ethanol as colorless prisms (3.5 g), mp>260° $[\alpha]^{28}_D = +58.6$ (C=0.2, CH$_3$OH).

(e) (S) Methyl-6-(1,2,3,4-tetrahydro-5,6 dimethoxy-2-naphthaleneamino) -6-oxo-hexanoate Methyl 5-(chloroformyl)pentanoate (1.8 g) was added dropwise to a stirred solution of the amine from step (c) (2.43 g) and triethylamine (2.8 mls) in dry dichloromethane (100 ml). The solution was heated under reflux for 1 hour. The cooled solution was washed with dilute hydrochloric acid, dilute sodium bicarbonate solution and brine. The organic phase was dried over magnesium sulfate filtered and evaporated to leave a colorless solid which crystallised from toluene/petrol ether as colorless flakes (3.2 g) mp 115°–116° $[\alpha]^{24}_D = -38.6$ (C=0.17 CH$_3$OH).

(f) (S) 6-(1,2,3,4-Tetrahydro-5,6-dimethoxy-2-naphthaleneamino) -6-oxo-hexanoic acid A solution of the ester from step (e) (3.0 g) in methanol (50 ml) and 10% sodium hydroxide solution (4 ml) was heated under reflux for 1 hour. The solution was evaporated, cooled and acidified with dilute hydrochloric acid. The precipitate was dissolved in chloroform, washed with brine, dried over magnesium sulfate, filtered and evaporated to leave a solid which crystallised from ethyl acetate/petroleum ether as colorless prisms (2.5 g) mp 147°–149° $[\alpha]^{24}_D = -40.7$ (C=0.15 CH$_3$OH).

(g) (R*,S*) - N,N'-Bis[1,2,3,4-tetrahydro-5,6-dimethoxy-2-napthyl]-hexane-1,6-diamide A solution of the acid from step (f) (1.1 g) and N,N'-carbonyldiimidazole (0.53 g) in dry dichloromethane was stirred at room temperature for 2 hours. A solution of the amine from step (d) (0.68 g) [free base] in dry dichloromethane (50 ml) was added and the mixture stirred at room temperature for 18 hours. The resulting precipitate was redissolved in chloroform and the organic phase washed with dilute hydrochloric acid, dilute sodium bicarbonate solution and brine. The organic phase was dried over magnesium sulfate filtered and evaporated to leave a colorless solid which was purified by filtering from hot methanol (1.37 g) mp 256°–258° $[\alpha]^{25}_D = \pm 0.1$ (C=0.14 CH$_3$OH/CHCl$_3$ 50/50)

(h) (R*S*) - N,N'-Bis[1,2,3,4-tetrahydro-5,6-dimethoxy-2-naphthyl]-hexane-1,6-diamine dihydrochloride A solution of the bis amide from step (g) (1.3 g) in dry tetrahydrofuran (400 ml) was stirred during the addition of borane in tetrahydrofuran (50 ml, 1M solution). The solution was heated under reflux in a nitrogen atmosphere for 24 hours. Methanol (200 ml) was added to the cooled solution and evaporation gave a sticky solid. Methanolic HCl was added and the suspension heated under reflux for 4 hours. The solution was evaporated to leave a colorless solid which crystallised from methanol as colorless prisms (1.19 g) mp>260° $[\alpha]^{25}_D = -0.5$ (C=0.2 H$_2$O).

(i) (R*S*) - 2,2'[2,6-Hexanediylbisamino]-bis-[1,2,3,4-tetrahydro-5,6-naphthalenediol]

A solution of the bis amine from step (h) (1.05 g) in 48% aqueous hydrobromic acid (50 ml) was heated under reflux for 2 hours in a nitrogen atmosphere. The solution was evaporated to dryness and the residue crystallised from methanol to give the title compound dihydrobromide as colorless prisms (0.70 g) mp>250° $[\alpha]^{28}_D = -1.2$ (±0.4) (C=0.18 H$_2$O).

Example 2

By analogous methods to those described in Example 1 above, the following compounds were made:

(a)

[R-(R*R*)]-2,2'-[1,6-Hexanediylbisamino]-bis-[1,2,3,4-tetrahydro-5,6-naphthalendiol]dihydrobromide mp>260° $[60]^{24}_D = +55.8$ (C=0.24, H$_2$O)

(b)

[S-(R*R*)]-2,2-[1,6-Hexanediylbisamino]-bis-[1,2,3,4-tetrahydro-5,6-naphthalenediol]dihydrobromide mp>260° $[\alpha]^{24}_D = -58.1$ (C=0.18, H$_2$O).

Example 3

2,2'-{1,6-Hexanediylbisamino)-bis-(1,2,3,4-tetrahydro-5,6-naphthalenediol)

(a) N,N'-Bis-(1,2,3,4-tetrahydro-5,6-dimethoxy-2-naphthyl) hexane-1,6-diamide A solution of adipoyl chloride (1.1 g, 0.006M) in chloroform (15 ml) was added dropwise to a solution of 1,2,3,4-tetrahydro-5,6-dimethoxy-2-aminonaphthalene (2.5 g, 0.012M) and triethylamine (1.4 g, 0.014M) in chloroform (15 ml). The mixture was stirred for 1 hour, quenched by addition of water and the organic phase was separated, washed with water and was dried over magnesium sulfate. The mixture was filtered and the filtrate was evaporated to dryness leaving a solid which was crystallised from methanol to give the required amide 2.0 g (63%) mp 223°–5°.

(b) N,N'-Bis-(1,2,3,4-tetrahydro-5,6-dimethoxy-2-naphthyl) hexane-1,6-diamine dihydrochloride A suspension of the amide from step (a) (2.0 g) was stirred under nitrogen at room temperature in dry tetrahydrofuran (250 ml) while 10 ml of a 1M borane/tetrahydrofuran complex was added from a syringe. The resulting mixture was heated at reflux for 3 hours, cooled, and a further 10 ml of the borane complex was added. The mixture was heated at reflux overnight during which time a clear solution formed. The mixture was cooled and methanol was added cautiously and the solution was evaporated to dryness. Methanol was added to the residue and the solution was boiled for 30 minutes. The solution was evaporated to dryness and the residue was dissolved in ether containing a few drops of ethanol. Excess ethereal hydrogen chloride was added to this solution and the precipitated solid was filtered off, washed well with hot ethanol and dried to give the required amine hydrochloride 1.9 g (87%) mp 280° (decomp).

(c) 2,2'-(1,6-Hexanediylbisamino)-bis-(1,2,3,4-tetrahydro-5,6-naphthalenediol) dihydrobromide A suspension of the dimethoxy amine from step (b) (1.8 g, 0.003M) in 48% aqueous hydrogen bromide (80 ml) was heated at reflux under nitrogen for 3 hours. Solution occurred briefly after 45 minutes but a white solid began to form almost immediately. After 3 hours the mixture was cooled and the solid was filtered off. It was washed with hot methanol, dissolved in methanol/water and the solution was treated with charcoal, filtered and the filtrate was evaporated to dryness. The title compound was obtained, as the dihydrobromide salt 1.1 g (57%) mp 250°.

Analysis

Found: C, 49.7; H, 6.1; N, 4.2; Br, 24.7% $C_{26}H_{36}N_2O_4$ requires with 1.5 mole $H_2O$ (4.3%) C, 49.6; H, 6.5; N, 4.4; Br, 25.4%

Example 4

By analogous methods to those described in Example 3 above, the following compound was made:

2,2'-(1,6-hexanediylbisamino)-bis-(1,2,3,4-tetrahydro-6,7-naphthalenediol) dihydrobromide mp>260°

Example 5

[R(R*, R*)](+)-7,7'-[1,6-Hexanediylbis(aminomethylene)]-bis (bicyclo[4.2.0]-octa-1,3,5-triene-2,3-diol)

(a) Synthesis and separation of the S-(−)-1-phenylethylamides of (+)-2,3-bis(phenylmethoxy)bicyclo[4.2.0]-octa-1,3,5-triene-7-carboxylic acid (±)-2,3-Bis-(phenylmethoxy)-bicyclo-[4,2,0]-octa-3,5-triene-7-carboxylic acid (40.0 g, 0.11 moles) in dry tetrahydrofuran (500 ml) was treated under nitrogen at 5° with N,N'-carbonyldiimidazole (20.8 g, 0.13 moles). The reaction mixture was kept at 5° for 3 hours and S-(−)-1-phenylethylamine (15.3 g, 0.125 moles) was added dropwise. The solution was maintained at 20° for 2 hours and then water and dichloromethane were added. The organic layer was separated, washed with dilute HCl, aqueous bicarbonate and brine, dried and evaporated to a solid (47.3 g). This amide mixture was separated by preparative high pressure liquid chromatography on silica using ethyl acetate/petroleum ether mixtures. Two fractions were obtained and recrystallised from ethyl acetate:

Less polar diastereomer: [S-(R*,S*)]-N-(1-phenylethyl) -2,3-bis(phenylmethoxy)-bicyclo-[4,2,0]-octa-1,3,5-triene-7-carboxamide, m.p. 186°–188°, $[\alpha]_D = +1.9°(c=0.3, CHCl_3)$, $\delta CH_3 (CDCl_3) = 1.39$ p.p.m.

More polar diastereomer: [S-(R*, R*)]-N-(1-phenylethyl) -2,3-bis-(phenylmethoxy)-bicyclo-[4.2.0]-octa-1,3,5-triene-7-carboxamide, m.p. 171°–173°, $[\alpha]_D = +25.6°$ (c=0.3, CHCl_3), $\delta CH_3 (CDCl_3) = 1.45$ p.p.m.

(b)
[S-(R*,S*)][-N-(1-Phenylethyl)-2,3-bis(phenylmethoxy)-bicyclo-[4,2,0]-octa-1,3,5-triene-7-methanamine hydrochloride The [S—(R*,S*)]-amide from step (a) above (13.2 g, 2.85 mmoles) in dry tetrahydrofuran (330 ml) under nitrogen was treated with 1M borane in tetrahydrofuran (140 ml, 140 mmoles) and boiled under reflux for 5 hours. After cooling methanol and methanolic hydrogen chloride were added and the mixture stirred overnight. The solvents were evaporated and the residue when triturated with dry ether gave the [S—(R*,S*)]-amine hydrochloride as white crystals (10.5 g), m.p. 171°–173°. $\delta(CDCl_3)$ 6.80(1H,d),6.60(1H,d).

(c)
[1S-[1R*[1R*[7S*(7S*)]]]]-N,N'-Bis-(1-phenylethyl)-N,N'-bis[(2,3-bis(phenylmethoxybicyclo[4,2,0]-octa-1,3,5-triene-7-yl]-methyl]-hexanediamide.

A solution of adipoyl chloride (0.915 g, 5 mmoles) in dichloromethane (40 ml) was added dropwise to a stirred solution of the above [S—(R*,S*)]-amine hydrochloride (4.84 g, 10 mmoles) from step (b) and triethylamine (3.03 g 30 mmoles) in dichloromethane (80 ml). The mixture was stirred at 20° overnight then poured into water. The organic phase was separated, washed with aqueous hydrochloric acid, aqueous sodium bicarbonate and brine, dried and evaporated to a colorless solid (4.8 g, m.p. 48°).

(d)
[1S-[1R*-[1R*[7S*(7S*)]]]]1,6-hexanediylbis-[N-(1-phenylethyl) -2,3-bis(phenylmethoxy)-bicyclo[4.2.0]-octa-1,3,5-triene-7-methanamine]dihydrochloride.

The [1S-[1R*-[1R*[7S*(7S*)]]]]-bis amide (4.86 g, 4.8 mmoles) in tetrahydrofuran (100 ml) was treated under nitrogen with 1M borane in tetrahydrofuran (24 ml, 24 mmoles) and then heated under reflux for 6 hours. After cooling methanol and methanolic hydrogen chloride were added and the solution stirred overnight and evaporated to dryness. The residue, on trituration with dry ether, gave the diamine dihydrochloride (4.6 g) which decomposes without melting above 90°.

(e) [R(R*, R*)](+)-7,7'-[1,6-Hexanediylbis(aminomethylene)]-bis(bicyclo[4.2.0]-octa-1,3,5-triene-2,3-diol)dihydrochloride.

The above [1S-[1R*[1R*[7S*(7S*)]]]]-diamine dihydrochloride (1 g) in ethanol (20 ml) and acetic acid (2 ml) containing 10% palladium on carbon catalyst (0.1 g) was shaken under 3 atmospheres of hydrogen at ambient temperature for 72 hours. The mixture was filtered and the filter cake extracted with hot water. Evaporation of the water gave the (+)-diamine dihydrochloride (0.3 g), m.p. 235° (decomp), $[\alpha^{30}_D = +12.4°$ (C=0.15,$H_2O$).

Example 6

By analogous methods to those described in Example 5 above, the following compounds were made:
(a) starting from the [S-(R*, R*)]amide of Example 5a,

[S-(R*, R*)]-7,7'-[1,6-hexanediylbis(aminomethylene)]bis(bicyclo[4.2.0]-octa-1,3,5-triene-2,3-diol dihydrochloride mp 235° (Decomp), $[\alpha]^{30}_D = -11.8$, (C=0.15, $H_2O$).
(b) starting from a mixture of the [S—(R*,S*)] and S—(R*, R*)] amides of Example 5a, racemic and meso (R*S*)-7,7'-[1,6-hexanediylbis(aminomethylene) -bis(bicyclo-[4.2.0]-octa-1,3,5-triene-2,3-diol]dihydrochloride mp 240° (decomposes).

Example 7

Racemic and meso (R*,S*)-7,7'-[1,6-hexanediylbis(aminomethylene)-bis(bicyclo-[4.2.0]-octa-1,3,5-triene-2,3-diol]

(a) Racemic and meso (R*S*)-N,N'-hexamethylene-bis-[2,3-bis(phenylmethoxy)bicyclo-[4.2.0]-octa-1,3,5-triene-7carboxamide]

2,3-Bis-(phenylmethoxy)-bicyclo-[4.2.0]-octa-1,3,5-triene-7-carboxylic acid (0.72 g) was dissolved in dry dichloromethane (40 ml) and cooled to −5° and triethylamine (0.31 ml) added. To this was added a solution of ethyl chloroformate (0.19 ml) in dry dichloromethane (2 ml) dropwise over 10 minutes. The solution was stirred at −5° for 1 hour and hexane-1,6-diamine (0.11 g) added and the mixture warmed to room temperature for 4 hours. The reaction mixture was washed with water, 2N hydrochloric acid, 2N sodium hydroxide solution and brine dried ($Na_2SO_4$) and evaporated. The residue was recrystallised from ethanol affording the purified bis amide (0.43 g) mp 155°–9°.

(b) Racemic and meso (R*,S*)-7,7'-[1,6-hexanediylbis(aminomethylene)-bis(bicyclo-[4.2.0]-octa-1,3,5-triene-2,3-diol] dihydrochloride The product of Example 7(a) was treated by the processes described in Examples 5(d) and 5(e) above, to give the title compound, as the dihydrochloride salt, m.p. 240° (decomposes).

Example 8

7-[6-(2-Phenylethylamino)hexylamino]methylbicyclo[4.2.0]-octa-1,3,5-triene-2,3-diol (a) N-(2-Phenylethyl)-N'-[[2,3-bis-(phenylmethoxy)bicyclo-[4.2.0]-octa-1,3,5-triene-7-yl]methyl]hexane-1,6-diamide A solution of 6-oxo-6-(2-phenylethylamino)hexanoic acid (1.25 g) and N,N'-carbonyldiimidazole (0.9 g) in dry dichloromethane (25 ml) was stirred at 20° for 2 h, and a solution of 2,3-bis(phenylmethoxy)bicyclo-[4.2.0]-octa-1,3,5-triene-7-methanamine hydrochloride (1.9 g) and triethylamine (0.5 g, 0.7 ml) in dry dichloromethane (20 ml) was then added. The mixture was stirred for 2.5 h at 20° and water (50 ml) added. The organic phase was separated, washed with dilute hydrochloric acid, aqueous sodium bicarbonate and brine, dried over $MgSO_4$ and evaporated leaving the required diamide as a colorless solid (2.3 g) m.p. 152°–155°.

(b) N-(2-Phenylethyl)-N'-[[2,3-bis(phenylmethoxy)bicyclo[4.2.0]-octa-1,3,5-triene-7-yl]methyl]-1,6-hexanediamine dihydrochloride The sub-title compound was prepared from the product of Example 8(a) using the method of Example 5(d) above, m.p. >250°.

(c) 7-[6-(2-Phenylethylamino)hexylamino]methylbicyclo 4.2.0]-octa-1,3,5-triene-2,3-diol dihydrochloride The title compound was prepared from the product of Example 8(b) above, as the dihydrochloride salt, using the method of Example 5(e), m.p. 208°–210°.

Example 9

By analogous methods to those described above in 8, the following compound was made:
7-[6-[2-(3,4-dihydroxyphenyl)ethylamino]hexylamino]methylbicyclo[4.2.0]-octa-1,3,5-triene-2,3-diol dihydrochloride, m.p. 217° (decomposes).

Example 10

7-[6-(2-Phenylethylamino)hexylamino]methylbicyclo[4.2.0]-octa-1,3,5-triene-3,4-diol (a) N-[(3,4-Dimethoxybicyclo-[4.2.0]-octa-1,3,5-triene-7-yl)methyl]-N'-(2-phenylethyl)hexane-1,6-diamide 6-Oxo-6-(2-phenylethylamino) hexanoic acid (8.65 g) was dissolved in dry tetrahydrofuran (220 ml) under an inert atmosphere and cooled to 0°–5° N,N-Carbonyldiimidazole (6.12 g) was added over 5 minutes, and the mixture stirred at 0.5° for 3 hours.
3,4-Dimethoxybicyclo-[4.2.0]-octa-1,3,5-triene-7-methylamine hydrochloride (7.98 g) and triethylamine (4.85 mls) were added successively, and the mixture was stirred at room temperature for 2 hours. The resulting white precipitate was collected by filtration, washed with dry ether and dried in vacuo at 50°. The product was crystallised from propan-2-ol to give a white solid, 8.77 g mp 150°–152°.

(b) N-[(3,4-Dimethoxybicyclo-[4.2.0]-octa-1,3,5-triene-7-yl)methyl]-N'-(2-phenylethyl)-hexane-1,6-diamine dihydrochloride A 1 molar solution of borane-tetrahydrofuran complex (75.5 ml) was added to a solution of the product of step (a) (8.0 g) in tetrahydrofuran (160 ml) under an inert atmosphere. The solution was heated at reflux overnight, cooled to room temperature, and methanol (50 ml) cautiously added. When all effervescence had ceased, methanolic hydrogen chloride (50 ml) was added, and the mixture refluxed for an hour. The suspension was reduced to dryness giving a white solid which was crystallised from aqueous ethanol to give white needles, 6.88 g mp 258°–9°.

(c) 7-[6-(2-Phenylethylamino)hexylamino]methylbicyclo 4.2.0]-octa-1,3,5-triene-3,4-diol dihydrobromide The product of step (b) (3.25 g) was dissolved in dry dichloromethane (10 ml) and cooled to −78°. Boron tribromide (3.5 ml) was added, and the solution stirred at −78° for 3 hours followed by 2 hours at room temperature. Methanol (about 25 ml) was added, and the mixture reduced to dryness. The resulting white solid was crystallised from dry methanol to give the title compound as the dihydrobromide salt, 2 HBr, m.p 210°–4° (dec).

Analysis: $C_{23}H_{32}N_2O_2$,
Theoretical: C=52.08%, H=6.42%, N=5.28%, Br=30.19%;
Found: C=51.69%, H=6.29%, N=5.11%, Br=30.16%.

Example 11

By analogous methods to those described in Examples 5 and 10 above, the following compounds were made:

(a)

(7,7'-[1,6-Hexanediylbis(aminomethylene)]-bis-bicyclo[4.2.0]-octa-1,3,5-triene-3,4-diol) dihydrobromide m.p. 226° (decomposes).

(b)

7-[6-[2-(3,4-Dihydroxyphenyl)ethylamino]hexylamino]-methylbicyclo [4.2.0]-octa-1,3,5-triene-3,4-diol dihydrobromide m.p. 100°–105°.

Example 12

4-[2-(6-(2-Phenylethylamino)hexylamino)ethyl]-1,2-benzenediol (a)

N-[2-(3,4-Dimethoxyphenyl)ethyl]-N'-[2-phenylethyl]-hexane-1,6-diamide

A solution of 6-oxo-6-(2-(3,4-dimethoxyphenyl)ethylaminohexanoic acid (9.3 g), and N,N'-carbonyldiimidazole (4.90 g) in dry dichloromethane (300 ml) was stirred at room temperature for 2 hours. A solution of 2-phenylethylamine (3.8 ml) in dichloromethane (50 ml) was added and the mixture stirred at room temperature for 3 hours.

The solution was washed with 2N HCl, water, 5% aqueous sodium bicarbonate solution and water. The organic phase was dried over magnesium sulfate, filtered and evaporated to leave a solid which crystallised from ethanol (11.38 g), m.p. 183°–184°.

(b)

N-[2-(3,4-Dimethoxyphenyl)ethyl]-N'-[2-phenylethyl]-hexane-1,6-diamine dihydrochloride A solution of the diamide product of step 12(a) (4.94 g) in dry tetrahydrofuran (150 ml) was stirred under a nitrogen atmosphere while diborane in tetrahydrofuran (48 ml of 1M solution) was added. The solution was heated under reflux for 24 hours.

Methanol (100 ml) was added to the cooled solution and the mixture evaporated to dryness. The residue was dissolved in methanolic HCl (100 ml) and heated under reflux for 1 hour. The solution was evaporated and the solid crystallised from methanol (4.90 g), mp 283°–285°.

(c)

4-[2-(6-(2-Phenylethylamino)hexylamino)ethyl]-1,2-benzenediol dihydrobromide

A solution of the diamine product of step (b) (4.75 g) in 48% aqueous hydrobromic acid (70 ml) was heated under reflux in an atmosphere of nitrogen for 3.5 hours. The solid which formed on cooling was filtered off and crystallised from ethanol, to give the title compound as the dihydrobromide salt, (3.1 g), mp 227°–228°.

Example 13

4-[2-(6-(2-(4-Aminophenyl)ethylamino)hexylamino)ethyl]-1,2-benzenediol (a)

N-[2-(3,4-Dimethoxyphenyl)ethyl]-N'-[2-(4-nitrophenyl)-ethyl]-hexane-1,6-diamide dihydrochloride The sub-title compound was prepared by the method of Example 12(b), mp 153°–155°.

(b)

N-[2-(3,4-Dimethoxyphenyl)ethyl]-N'-[2-(4-aminophenyl) ethyl]-hexane-1,6-diamine trihydrochloride A solution of the product of step (b) (1 g) was dissolved in a mixture of ethanol (50 ml) and acetic acid (25 ml) and hydrogenated at 45 p.s.i. and room temperature over a palladium catalyst. After hydrogen uptake had ceased the reaction mixture was warmed and filtered to remove the catalyst. The filtrate was evaporated to dryness and a solution of hydrogen chloride gas in methanol added. The solution obtained was evaporated to dryness and the solid triturated with ether (0.8 g) mp > 250°.

(c)

4-[2-(6-(4-Aminophenyl)ethylamino)hexylamino)ethyl]-1,2-benzenediol trihydrobromide The title compound was made as the trihydrobromide salt from the product of step (b) by the process described in Example 12(c) above, mp > 250°.

Example 14

4-[2-(6-(2-(4-Chlorophenyl)ethylamino)hexylamino)ethyl]-1,2-benzenediol (a)

N-[2-(3,4-Dimethoxyphenyl)ethyl]-N'-[2-(4-chlorophenyl)ethyl]-hexane-1,6-diamide The sub-title compound was prepared using the method of Example 12(a), mp 167°–169°.

(b)

N-[2-(3,4-Dimethoxyphenyl)ethyl]-N'-[2-(4-chlorophenyl)ethyl]-hexane-1,6-diamine The sub-title compound was prepared using the method of Example 12(b), mp > 260°.

(c)

4-[2-(6-(2-(4-Chlorophenyl)ethylamino)hexylamino)-ethyl]-1,2-benzenediol dihydrobromide The title compound was prepared, as the dihydrobromide salt, using the method of Example 12(c), mp 172°–174°.

Example 15

By analogous methods to those described in Examples 12, 13 and 14 above, the following compounds were made:-
(a) 4-[2-(6-phenylamino)hexylamino)ethyl]-1,2-benzenediol dihydrobromide, mp 216°–218°.
(b) 4-[2-(6-phenylmethylamino)hexylamino)ethyl]-1,2-benzenediol dihydrobromide, mp 176°–178°.
(c) 4-[2-(6-(3-phenylpropylamino)hexylamino)ethyl]-1,2-benzenediol dihydrobromide, mp 158°–160°.
(d) 4-[2-(6-(4-phenylbutylamino)hexylamino)ethyl]-1,2-benzenediol dihydrobromide, mp 196.5°–199°.
(e) 4-[2-(6-amino-hexylamino)ethyl]-1,2-benzenediol dihydrobromide, mp 201°–202°.

(f)

4-[2-(6-(di-n-propylamino)hexylamino)ethyl]-1,2-benzenediol dihydrobromide, mp 164°–165°.

(g) 4-[2-(6-(N-methyl(2-phenylethylamino)hexylamino)-ethyl]-1,2-benzenediol dihydrobromide, mp 167°–169°.
(h) 4-[2-(6-(2-phenylpropylamino)hexylamino)ethyl]-1,2-benzenediol dihydrobromide, mp 135°–137°.

(i) 4-[2-(6-(2-(4-nitrophenyl)ethylamino)hexylamino)ethyl]-1,2-benzenediol dihydrobromide, mp 164° dec.
(j) 4-[2-(6-(2-(4-hydroxyphenyl)ethylamino)hexylamino)-ethyl]-1,2-benzenediol dihydrobromide, mp > 260°.
(k) 4-[2-(6-(2-(4-methylphenyl)ethylamino)hexylamino)ethyl]-1,2-benzenediol dihydrobromide, mp 195° dec.
(l) 4-[2-(6-(2-(4-pyridinyl)ethylamino)hexylamino)ethyl]-1,2-benzenediol trihydrobromide, mp 197°–8°.
(m) 4-[2-(6-(4-methylpiperazinyl)hexylamino)ethyl]-1,2-benzenediol trihydrobromide, mp 197°–198°.
(n) 4-[2-(N-methyl-6-(4-methylpiperazinyl)hexylamino) ethyl)-1,2-benzenediol trihydrobromide, mp 187°–190°.
(o) 4-[2-(4-(2-phenylethylamino)butylamino)ethyl]-1,2-benzenediol dihydrobromide mp 251°–5° (dec).
(p) 4-[2-(6-(1,2,3,4-tetrahydro-2-naphthylamino)hexylamino) ethyl]-1,2-benzenediol dihydrobromide mp 224°–6°.
(q) 4-[2-(8-(2-phenylethylamino)octylamino)ethyl]-1,2-benzenediol dihydrobromide mp 229°–30°.
(r) 4-[2-(5-(2-phenylethylamino)pentylamino)ethyl]-1,2-benzenediol dihydrobromide mp 187°–9°.
(s) 3-[6-(2-(3,4-dihydroxyphenyl)ethylamino)hexyl]1-phenyl-2,3,4,5-tetrahydro-1H-3-benzazepin-7,8-diol dihydrobromide mp 115° (dec).
(t) 4-[2-(N-methyl-6-(N'-methyl-2-phenylethylamino) hexylamino)ethyl]-1,2-benzenediol dihydrobromide mp 186°–8°.

Example 16

4-[2-(6-(2-Hydroxy-2-phenylethylamino)hexylamino)ethyl]-1,2-benzenediol

A solution of N-(2-hydroxy-2-phenylethyl)-N'-[2-(3,4-bis(phenylmethoxy)phenyl)ethyl]hexane-1,6-diamide prepared in an analogous manner to that described in Example 12(a) above (3.48 g) in dry tetrahydrofuran (100 ml) was stirred under a nitrogen atmosphere whilst diborane in tetrahydrofuran (30 ml of 1M solution) was added and then the solution heated to reflux for 6 hours. Methanol (100 ml) was added to the cooled solution and the mixture evaporated to dryness. The residue was dissolved in methanolic HCl (100 ml) and heated to reflux for 18 hours. The solution was evaporated to dryness and the residue recrystallised from ethanol to give the title compound, as the dihydrochloride salt, colorless prisms (1.3 g) mp 188°–9°.

Example 17

4-[2-(N-Methyl-6-(di-n-propylamino)hexylamino)ethyl]-1,2-benzenediol (a)

N-[2-(3,4-Dimethoxyphenyl)ethyl]-N-Methyl-N',N'-di-n-propyl-hexane-1,6-diamide

A solution of N-[2-(3,4-dimethoxyphenyl)ethyl]-N'N-di-n-propyl-hexane-1,6-diamide (3.9 g) in dry dimethyl formamide (20 ml) was added to a suspension of oil free sodium hydride (0.24 g) in dry dimethylformamide (20 mls). The mixture was heated at 70° for 1 hour. Methyl iodide (0.75 mls) was added to the cooled suspension and the mixture stirred at room temperature for 2 hours.

The mixture was evaporated to dryness, dissolved in ethyl acetate and the organic phase washed with dilute hydrochloric acid, dilute sodium bicarbonate solution and brine. The organic phase was dried over magnesium sulfate, filtered and evaporated to leave a brown oil (3.8 g) M+406.

(b)

N-[2-(3,4-Dimethoxyphenyl)ethyl]-N-methyl-N',N'-di-n-propyl-hexane-1,6-diamine dihydrochloride The sub title compound was prepared from the product of step (a) by the method of Example 12(b) above, mp 130°–132°.

(c) 4-[2-(N-Methyl-6-(-di-n-propylamino)hexylamino) ethyl]-1,2-benzenediol dihydrobromide The title compound was prepared, as the dihydrobromide salt, from the product of step (b) by the method of Example 12(c) above, mp 97°–99°.

Example 18

±-4-[2-[4-Hydroxy-6-(2-phenylethylamino)-hexylamino]ethyl]-1,2-benzenediol (a)

N-(2-Phenylethylamino)-tetrahydro-5-oxo-2-furanacetamide

Ethyl chloroformate (4.15 g, 3.7 ml) was added dropwise with stirring to a solution of tetrahydro-5-oxo-2-furanacetic acid (5.5 g) and triethylamine (3.8 g, 5.3 ml) in dry dichloromethane (75 ml) at −10° and the mixture stirred for 45 minutes. 2-Phenylethylamine (4.6 g) in dry dichloromethane (25 ml) was added and the reaction kept at 20° for 18 h. The solution was washed with sodium bicarbonate solution, hydrochloric acid and water, dried (MgSO4) and evaporated giving the required lactone-amide (3.5 g) as a pale cream solid mp 83°–85° after trituration with ether.

(b)

3-Hydroxy-N'-2-(3,4-dimethoxyphenyl)ethyl]-N-[2-phenylethyl]hexane-1,6-diamine

The lactone-amide from step (a) (3.45 g) and 2-(3,4-dimethoxyphenyl)ethylamine (2.54 g) were heated together at 100° under nitrogen for 1 hour. The melt was cooled and triturated with ether and the resulting solid recrystallised from ethanol to give the required diamide (5.1 g) mp 158°–160°.

(c)

6-[2-(3,4-Dimethoxyphenyl)ethylamino]-1-[2-phenylethylamino]-3-hexanol dihydrochloride The diamide from step (b) above (3.4 g) in dry tetrahydrofuran (150 ml) was treated with 1M boranetetrahydrofuran (40 ml) under nitrogen and boiled under reflux for 4 hours. The solution was cooled, methanol (25 ml) added, and the whole evaporated to dryness. The residue was taken up in methanol (50 ml) and saturated methanolic hydrogen chloride (50 ml) and stirred at 20° for 18 h. The solvent was evaporated and the residue triturated with ether giving the dihydrochloride (2.7 g) as a white solid, which decomposes without melting above 240°.

(d)

4-[2-[4-hydroxy-6-(2-phenylethylamino)-hexylamino]ethyl]-1,2-benzenediol dihydrobromide The dihydrochloride from step (c) (2.2 g) in dry dichloromethane (100 ml) was treated with triethylamine (1.3 ml, 0.94 g) and stirred under nitrogen for 15 minutes. The resulting suspension was cooled to −70°, boron tribromide (2.2 ml, 5.85 g) added and the mixture allowed to warm to ambient temperature with stirring over 18 hours. Methanol (10 ml) was added, the resulting solution evaporated to dryness and the solid residue recrystallised from 2-propanol giving the title compound (2.2 g), as the dihydrobromide salt, colorless needles mp 137°–139°.

Example 19

4-[2-[6-[2-(4-Chlorophenyl)ethylamino]hexylamino]-ethyl]-1,2-benzenediol dihydrochloride 4-[2-[6-[2-(4-Chlorophenyl)-ethylamino]hexylamino]-ethyl]-1,2-benzenediol dihydrobromide (3.0 g) was dissolved in the minimum amount of water and saturated sodium bicarbonate was added until the pH of the solution was about 8. The precipitated free base was washed with ice cold water and then suspended in concentrated hydrochloric acid and stirred with gentle warming until all the sticky material had been replaced by a fine white solid. The suspension was cooled in ice and filtered and the precipitate recrystallised from ethanol to give the title dihydrochloride (2.0 g) as white crystals mp 186°–188°.

Found Cl: 23.02%, dihydrochloride requires Cl: 22.93%.

Example 20

4-[2-[6-(2-Phenylethylamino)hexylamino]ethyl]-1,2-benzenediol dihydrochloride

The title compound was prepared from the corresponding dihydrobromide salt by the method of Example 19, mp 219°–219.5°.

Example 21

1,2,3,4-Tetrahydro-2-[6-(2-phenylethyl)aminohexyl-]amino-5,6-naphthalenediol (a) 6-Oxo-6-(2-phenylethylamino)hexanoic acid Adipic acid monomethyl ester (24 g, 0.15 mole) was dissolved in dry dichloromethane (500 ml) and cooled in ice-water, triethylamine (22.3 ml, 0.16 mole) was added followed by a solution of ethylchloroformate (14.3 ml, 0.15 mole) in dichloromethane (50 ml) which was added over a period of 30 minutes. The resulting suspension was stirred for 30 minutes and a solution of 2-phenylethylamine (18.8 ml, 0.16 mole) in dichloromethane (50 ml) added over a period of 30 minutes and the resulting mixture stirred at room temperature for 2 hours. The reaction mixture was washed with 2N aqueous hydrochloric acid (2×200 ml), 10% aqueous sodium carbonate solution (200 ml) and water and evaporated in vacuo affording the crude amido ester. This solid was heated to reflux with a solution of potassium hydroxide (9.52 g, 0.17 mole) in water (300 ml) for 1 hour. The cooled solution was washed with ether (200 ml), acidified and the solid isolated by filtration and dried in vacuo affording the required amido acid (26.1 g) mp 113°–4°. The crude acid was purified by recrystallisation from ethyl acetate (mp 114°–6°).

(b) N-[1,2,3,4-Tetrahydro-5,6-dimethoxy-2-naphthyl]-N'-[2-phenylethyl]hexane-1,6-diamide A solution of 6-oxo-6-(2-phenylethylamino)hexanoic acid (2.49 g) and carbonyldiimidazole (1.62 g) in dry dichloromethane (100 ml) was stirred under a nitrogen atmosphere for 2 hours at room temperature. A solution of 1,2,3,4-tetrahydro-5,6-dimethoxy-2- aminonaphthalene (2.07 g) in dichloromethane (20 ml) was added and the solution stirred at room temperature for 18 hours. The solution was washed with dilute hydrochloric acid, dilute sodium carbonate solution and water. The organic phase was separated, dried over magnesium sulfate, filtered and evaporated to leave the sub-title compound which crystallised from isopropanol as colorless flakes (3.8 g), m.p. 191°–193°.

(c) N-[1,2,3,4-Tetrahydro-5,6-dimethoxy-2-naphthyl]-N'-[2-phenylethyl]hexane-1,6-diamine dihydrochloride A solution of the product of step (b) (3.5 g) and borane-tetrahydrofuran complex (32 mls) in dry tetrahydrofuran (200 ml) was heated under reflux under a nitrogen atmosphere for 24 hours.

The solution was cooled, methanol (100 mls) added and the solution evaporated to dryness. A solution of the residue in methanolic/HCl was heated under reflux for 5 hours. The solution was evaporated to leave a solid which crystallised from methanol as colorless prisms (2.3 g), m.p. 265°.

(d) 1,2,3,4-Tetrahydro-2-[6-(2-phenylethyl)aminohexyl]-amino-5,6-naphthalenediol dihydrobromide A solution of the product of step (c) (2 g) in aqueous hydrobromic acid (20 ml) was heated at reflux under a slow stream of nitrogen for 4 hours. The solution was evaporated to dryness and the residue crystallised from ethanol to give the title compound, as the dihydrobromide salt, as colorless prisms (2.0 g), m.p. 240°–242°.

Example 22

1,2,3,4-Tetrahydro-2-[6-(2-(3,4-dihydroxyphenyl)-ethyl) aminohexyl]amino-5,6-naphthalenediol.

(a) N-[1,2,3,4-Tetrahydro-5,6-dimethoxy-2-naphthyl]-N'-2-(3,4-dimethoxyphenyl)ethylhexane-1,6-diamide The sub-title compound was prepared by the method of Example 21(a), m.p. 172°–174°.

(b) N-[1,2,3,4-Tetrahydro-5,6-dimethoxy-2-naphthyl]-N'-[2-(3,4-dimethoxyphenyl)ethyl]hexane-1,6-diamine dihydrochloride The sub-title compound was prepared from the product of step (a), by the method of Example 21(b), m.p. 260°.

(c) 1,2,3,4-Tetrahydro-2-[6-(2-(3,4-dihydroxyphenyl)-ethyl)aminohexyl]amino-5,6-naphthalenediol dihydrobromide The title compound was prepared from the product of step (b), as the dihydrobromide salt, by the method of Example 21(c), m.p. 270°.

Example 23

By analogous methods to those described in Example 21 above, the following compounds were made:
(a) 1,2,3,4-Tetrahydro-2-[6-(2-(3,4-dihydroxyphenyl)ethyl) aminohexyl]amino-6,7-naphthalenediol dihydrobromide, mp 258°–260°.
(b) 1,2,3,4-Tetrahydro-2-[6-(2-phenylethyl)aminohexyl]amino-6,7-naphthalenediol dihydrobromide, mp 266°–268°.

(c) 1,2,3,4-Tetrahydro-2-[4-(2-phenylethyl)aminobutyl]amino-5,6-naphthalenediol dihydrobromide, mp>250°.

(d) 1,2,3,4-Tetrahydro-2-[8-(2-phenylethyl)aminooctyl]amino-5,6-naphthalenediol dihydrobromide, mp 248°-252°.

(e) 1,2,3,4-Tetrahydro-2-[8-(2-(3,4-dihydroxyphenyl)ethyl)aminooctyl]amino-5,6-naphthalenediol dihydrobromide, mp 260.

(f) 1,2,3,4-Tetrahydro-2-[6-(2-phenylethyl)amino]hexylamino-5-naphthalenol dihydrobromide, mp 280° (dec).

Example 24

N,N'-Bis-(1,2,3,4-tetrahydro-5,6-dimethoxy-2-naphthyl)hexane-1,6-diamine dihydrochloride 1,2,3,4-Tetrahydro-5,6-dimethoxy-2-naphthalenamine hydrochloride (4.87 g) in acetonitrile (100 ml) was added slowly to a stirred suspension of potassium carbonate (3.0 g) in a refluxing solution of 1,6-dibromohexane (2.44 g) in acetonitrile (100 ml) over a period of 1 hour. When the addition was complete, reflux was continued for 24 hours, the solution filtered to remove inorganic salts, and the filtrate evaporated in vacuo to give an oil. Chromatography on silica, eluting with chloroform: methanol 95: 5, gave, following trituration with ethereal hydrogen chloride, the title compound 1.15 g (20%), mp 275° (decomp)

Example 25

4-[2-(6-(2-Phenylethylamino)hexylamino)ethyl]-1,2-benzenediol-bis-(2-methylpropionate) dihydrochloride Isobutyryl bromide (12 g) was added to a stirred solution of 4-[2-(6-(2-Phenylethylamino)hexylamino)ethyl]-1,2-benzenediol dihydrobromide (4 g) in trifluoracetic acid (100 ml). The solution was then stirred at room temperature for 24 hours. The excess solvent was evaporated and the residue treated with sodium bicarbonate solution. The basic mixture was thoroughly extracted with chloroform. The organic phase was separated, dried over magnesium sulfate, filtered and evaporated to leave a colorless oil which gave a white precipitate when treated with ethereal HCl. The white precipitate was recrystallised to give the title compound from ethanol as colorless prisms (2.8 g), m.p. 232°-234°.

Example 26

By analogous methods to those described in Example 25, the following compounds were made:

(a) 4-[2-(6-(2-phenylethylamino)hexylamino)ethyl]-1,2-benzenediol-bis-benzoate dihydrochloride, mp 230° (dec).

(b) 4-[2-(6-(2-phenylethylamino)hexylamino)ethyl]-1,2-benzenediol-bis-acetate dihydrobromide, mp 229°-230°.

Example 27

Bis(Phenylmethoxy)N-[2-(3,4-dihydroxyphenyl)ethyl]N'-[2-phenylethyl]-1,6-hexanediyl bis carbamate A suspension of 4-[2-(6-(2-phenylethylamino) hexylamino)ethyl]-1,2- benzenediol (4.2 g) in 10% aqueous borax solution (4 g in 40 ml) was adjusted to pH9 with 2N sodium hydroxide solution. The suspension was stirred for 4 hours. Benzylchloroformate (2.2 ml) was added and the mixture stirred at room temperature for 2.5 hours.

The suspension was acidified and the aqueous phase extracted with ether. The organic phase was separated, dried over magnesium sulfate, filtered and evaporated to leave an oil. The oil was purified by chromatography on silica gel eluting with dichloromethane/5% $CH_3OH$ to give the title compound, as a pale yellow oil (2.0 g) MS m/e 624.

| Example A Pharmaceutical Formulations Intravenous formulations | |
|---|---|
| 1. Compound of Example 12 | 1% w/v |
| Sodium metabisulphite | 1% w/v |
| Sodium chloride | 0.106% w/v |
| Water | to 100% |
| 2. Compound of Example 12 | 1% w/v |
| Sodium metabisulphite | 0.1% w/v |
| Sodium edetate | 0.01% w/v |
| Sodium chloride | qs to make isotonic |
| Water | to 100% |
| 3. Compound of Example 12 | 1% w/v |
| Sodium hydrogen phosphate | 0.94% w/v |
| Sodium phosphate | 0.24% w/v |
| Sodium chloride | 0.295% w/v |
| Water | to 100% |

We claim:

1. A compound of formula I,

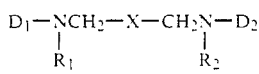

in which $D_1$ represents a group of formula II,

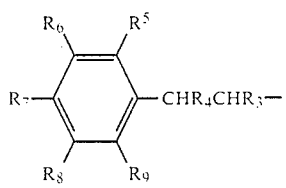

where $R_1$ represents hydrogen or alkyl $C_1$ to $C_8$,
$R_2$ represents hydrogen or alkyl $C_1$ to 8,
$R_3$, $R_4$, and $R_5$ are each hydrogen,
an adjacent pair of $R_6$, $R_7$, $R_8$ and $R_9$ represent hydroxy and the remainder represent hydrogen,
X represents a chain $-(CH_2)_n-$,
n is an integer from 3 to 5 inclusive,
$D_2$ represents alkyl $C_1$ to 8 substituted by phenyl; or alkyl $C_1$ to 8 substituted by phenyl which in turn is substituted by halogen, alkyl $C_1$ to 8, amino alkoxy $C_1$ to 8, or nitro,
or $D_2$ represents a group of formula III,

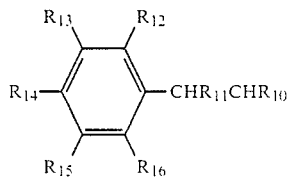

where $R_{10}$ and $R_{12}$ form a chain $-CH_2CH_2-$,
$R_{11}$ represents hydrogen or alkyl $C_1$ to 8,
$R_{13}$, $R_{14}$, $R_{15}$ and $R_{16}$ represent hydrogen,
and pharmaceutically acceptable derivatives thereof.

2. A compound according to claim 1, wherein $R_7$ is hydroxy.

3. A compound according to claim 1 selected from the group consisting of:

4-[2-(6-(2-phenylethylamino)hexylamino)ethyl]-1,2-benzenediol

4-[2-(6-(2-(4-aminophenyl)ethylamino)hexylamino)ethyl]-1,2-benzenediol

4-[2-(6-(2-(4-chlorophenyl)ethylamino)hexylamino)ethyl]-1,2-benzenediol

4-[2-(6-(3-phenylpropylamino)hexylamino)ethyl]-1,2-benzenediol

4-[2-(6-(4-phenylbutylamino)hexylamino)ethyl]-1,2-benzenediol

4-[2-(6(N-methyl(2-phenylethylamino)hexylamino)ethyl]-1,2-benzenediol

4-[2-(6-(2-phenylpropylamino)hexylamino)ethyl]-1,2-benzenediol

4-[2-(6-(2-(4-nitrophenyl)ethylamino)hexylamino)ethyl]-1,2-benzenediol

4-[2-(6-(2-(4-methylphenyl)ethylamino)hexylamino)ethyl]-1,2-benzenediol

4-[2-(6-(1,2,3,4-tetrahydro-2-naphthylamino)-hexylamino)ethyl]-1,2-benzenediol

4-[2-(5-(2-phenylethylamino)pentylamino)ethyl]-1,2benzenediol

4-[2-(N-methyl-6-(N'-methyl-2-phenylethylamino)-hexylamino)ethyl]-1,2-benzenediol and pharmaceutically acceptable acid addition salts thereof.

4. A compound according to claim 1 which is 4-[2-(6-(2-Phenylethylamino)hexylamino)ethyl]-1,2-benzenediol, or a pharmaceutically acceptable acid addition salt thereof.

5. A method of treatment of congestive heart failure which comprises administering an effective amount of a compound according to claim 1 to a patient suffering from such a condition.

* * * * *